(12) United States Patent
Leuenberger et al.

(10) Patent No.: US 6,444,227 B1
(45) Date of Patent: Sep. 3, 2002

(54) PROCESS FOR PREPARING FAT SOLUBLE BEADLETS

(75) Inventors: Bruno Leuenberger, Allschwil (CH); Jean-Claude Tritsch, Saint-Louis (FR); Johann Ulm, Oberwil (CH)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/626,976

(22) Filed: Jul. 27, 2000

(30) Foreign Application Priority Data

Aug. 5, 1999 (EP) .............................. 99115458

(51) Int. Cl.⁷ .......................... A61K 9/14; A61K 9/16; A61K 31/355; A61K 31/07
(52) U.S. Cl. ...................... 424/489; 424/484; 424/490; 514/458; 514/725
(58) Field of Search ............................... 424/489, 434, 424/484, 490; 264/4.3; 430/2; 514/458, 725

(56) References Cited

U.S. PATENT DOCUMENTS

| | | | |
|---|---|---|---|
| 4,670,247 A | * | 6/1987 | Scialpi ..................... 424/484 |
| 5,126,328 A | | 6/1992 | Bower et al. |
| 5,230,969 A | * | 7/1993 | Savant et al. ................ 430/2 |
| 6,030,645 A | | 2/2000 | Tritsch et al. |
| 6,039,901 A | * | 3/2000 | Soper et al. ................ 264/4.3 |

FOREIGN PATENT DOCUMENTS

| | | |
|---|---|---|
| EP | 0 285 682 A1 | 10/1988 |
| EP | 0 867 177 A1 | 2/1998 |
| EP | 0 982 038 A1 | 3/2000 |
| GB | 993138 | 5/1965 |

OTHER PUBLICATIONS

Patent Abstracts of Japan, vol. 17, No. 382 of JP 05065457 (1993).
Patent Abstracts of Japan, vol. 7, No. 268 of JP 58149645 (1983).
Cortesi, et al., "Sugar cross–linked gelatin for controlled release: microspheres and disks," *Biomaterials*, vol. 19, pp. 1641–1649 (1998).
Derwent English language abstract of EP 0 982 038 A1 (document B3).

* cited by examiner

Primary Examiner—Christopher R. Tate
Assistant Examiner—Randall Winston
(74) Attorney, Agent, or Firm—Bryan Cave LLP

(57) ABSTRACT

The invention relates to a process for preparing beadlets containing fat soluble substances in a gelatin matrix which comprises crosslinking the gelatin by radiation or enzymatically. Specifically, the invention relates to a process for preparing beadlets containing fat soluble substances having the steps of:

(1) forming an aqueous emulsion of a fat soluble substance, a gelatin, a reducing agent;
(2) converting the emulsion into a dry powder; and
(3) crosslinking the gelatin matrix in the coated particles by exposing the coated particles to radiation or, in the case of a crosslinking enzyme being present, by incubating the coated particles.

20 Claims, No Drawings

PROCESS FOR PREPARING FAT SOLUBLE BEADLETS

FIELD OF THE INVENTION

The invention is related to a process for preparing beadlets containing fat soluble substances.

BACKGROUND OF THE INVENTION

U.S. Pat. No. 4,670,247 reportedly discloses the preparation of fat soluble beadlets by emulsifying a fat soluble substance selected from the group consisting of vitamin A, D, E, K and derivatives thereof, carotenoids, polyunsaturated fatty acids, the flavoring or aroma substances with water, gelatin and a sugar. The emulsion is then converted to droplets. The droplets are collected in a starchy collecting powder to form particles. The particles from the starchy collecting powder are then heat treated to form a water insoluble beadlet. The selected fat soluble substance is preferably vitamin A acetate or vitamin A palmitate. The sugar is a reducing sugar and can be selected from the group consisting of fructose, glucose, lactose, maltose, xylose, and mixtures thereof. The collecting powder used according to U.S. Pat. No. 4,670,247 is a starchy powder. However, other powders such as, e.g., calcium silicate (EP 0 867 177 A), calcium aluminum silicate, tri-calcium phosphate, silicic acid or celluloses can also be used. The heat treatment results in crosslinking of the gelatin matrix.

According to conventional heating methods, the crosslinking step was performed by heating on preheated stainless steel trays in an electric oven at a temperature of from about 90° C. for 2 hours to about 180° C. for less than a minute. These conventional crosslinking methods by heating have the disadvantage that the crosslinking is not uniform due to the non-uniformity of the heat treatment. Moreover, the previous processes are often less satisfactory because too much energy is expended in their performance and thus they are uneconomical.

It has now been found that these disadvantages can be overcome when the crosslinking step is performed by exposure to radiation or by using an enzyme.

SUMMARY OF THE INVENTION

The present invention relates to a process for preparing beadlets containing fat soluble substances having the steps of:

(1) forming an aqueous emulsion of a fat soluble substance, a gelatin, and a reducing agent and, optionally, an antioxidant and/or a humectant;

(2) optionally adding a crosslinking enzyme;

(3) converting the emulsion into a dry powder; and (4) crosslinking the gelatin matrix in the coated particles by exposing the coated particles to radiation or, in the case of a crosslinking enzyme being present, by incubating the coated particles.

DETAILED DESCRIPTION OF THE INVENTION

As used herein, the term "fat soluble substance" refers to vitamins selected from the group consisting of vitamin A, D, E, K, and derivatives thereof, carotenoids, polyunsaturated fatty acids and flavoring or aroma substances as well as mixtures thereof. A preferred fat soluble substance is vitamin A and its derivatives, preferably vitamin A acetate or vitamin A palmitate. Suitable carotenoids include beta-carotene, astaxanthin, apocarotenal, canthaxanthin, apoester, citranaxanthin, zeaxanthin, lutein, and lycopenes, as well as mixtures thereof. Examples for polyunsaturated fatty acids include linoleic acid, linolenic acid, arachidonic acid, docosahexaenic acid, eicosapentaenic acid, and the like, as well as mixtures thereof.

As used herein, the term "reducing agent" refers to reducing sugars or reducing sugar derivatives. Preferred reducing sugar compounds are the monosaccharides, preferably pentoses and hexoses, and the oligosaccharides, preferably disaccharides. Examples of monosaccharides are glucose, fructose, galactose, mannose, talose, and invert sugar (mixture of glucose and fructose) as hexoses and arabinose, ribose and xylose as pentoses, threose as tetrose and glycerinaldehyde as triose. Examples of oligosaccharides are lactose, maltose, and the like. In addition, high fructose corn syrups (mixtures of fructose and dextrose) may also be employed in the practice of the invention.

As used herein, the term "antioxidant" includes butylated hydroxy anisole (BRA), butylated hydroxy toluene (BHT), ethoxyquin (6-ethoxy-1,2-dihydro-2,2,4-trimethylquinoline), tocopherols, and the like.

As used herein, the term "humectant" includes glycerol, sorbitol, polyethylene glycol, propylene glycol, and the like.

As used herein, the term "radiation" refers to any radiation source that will induce a reaction between the carbonyl group of the sugar with the free amino moiety of the gelatin molecule. Suitable radiation sources are light radiating in a range selected from the ultraviolet, visible, infrared or electromagnetic radiation sources such as microwaves.

As used herein, the term "microwaves" refers to electromagnetic waves having frequencies in the range of about 900 MHz to about 2.45 GHz. These waves are readily absorbed by dielectrics having a polar radical such as water. When such a dielectric is exposed to microwave energy at about 700 to about 1000 watts, its molecules are subjected to high-speed internal vibration which results in the generation of heat.

The crosslinking process is preferably carried out by microwave heating that provides a highly efficient heating and crosslinking effect. The beadlets crosslinked by applying microwave energy are insoluble in water and possess high stability, especially in feed production processes like extrusion and pelleting.

As used herein, the term "crosslinking enzyme" refers to transferases, particularly transglutaminases, which couple amino acids through the formation of a peptide bond. Thus, a reaction between the carbonyl group of the sugar with the free amino moiety of the gelatin molecule is catalyzed. A suitable transglutaminase is on the market under the trade name of ACTIVA TI® (Ajinomoto). The amount of the transglutaminase to be used is about 0.01 g/g to about 0.10 g/g gelatin.

Small quantities of other ingredients, e.g., emulsifiers, such as lecithin, extenders and solubilizers, and coloring agents can also be incorporated in the emulsions of this invention, as well as other excipients.

The first step of the process according to the invention involves emulsifying the fat soluble substance with water, gelatin and a reducing agent, and optionally with an antioxidant and/or a humectant.

The fat soluble substance can be present in an amount of about 1 wt % to about 80 wt %, preferably about 5 wt % to about 40 wt %.

Gelatin of any origin may be employed. Preferred gelatin is from pig or cattle, and have a Bloom No. of from 80 to 160, particularly 140. The gelatin may be present in an amount of about 5 wt % to about 70 wt %, preferably about 20 wt % to about 60 wt %.

The reducing agent can be present in an amount of about 2 wt % to about 20 wt %, preferably about 5 wt % to about 10 wt %.

The antioxidant can be present in an amount of about 2 wt % to about 15 wt %, preferably about 5 wt % to about 10 wt %.

The humectant can be present in an amount of about 2 wt % to about 20 wt %, preferably about 5 wt % to about 10 wt %.

The preparation of the emulsion can be carried out by methods that will be apparent to those skilled in the art. For example, the gelatin is dissolved in water with the aid of moderate heating, and the fat soluble substance is then dispersed or emulsified in the solution of the gelatin. The reducing agent, as well as any other ingredients, can be introduced into the mixture either before or after adding the fat soluble substance. The mixture is agitated until all dispersoids are uniformly distributed and, if necessary, by passing the mixture through a homogenizer.

The emulsion is then dried by known methods, e.g., by spray drying such as spraying into a collecting powder. In case of enzymatically crosslinking, the enzyme is added just before spraying the emulsion into the collecting powder. The particles containing the fat soluble substance formed in the collecting powder by known methods should be dried to a moisture content of less than 10%.

The crosslinking of the gelatin matrix in the coated particles is started either by exposure to radiation or by an enzyme being present during incubation.

With respect to the beadlet compositions containing an enzyme, the crosslinking of the coated particles is carried out by incubating the enzyme at temperatures where the enzyme is stable, e.g., up to 40° C. If appropriate, the enzymatically crosslinking procedure may be followed by treating as disclosed in U.S. Pat. No. 4,670,247. The enzymatic crosslinking process leads to less thermal stress of the active ingredient. Furthermore, the crosslinking reaction results in a homogeneously crosslinked product.

The crosslinking process induced by microwaves is carried out under stirring, usually in a microwave oven, e.g., at 1000 Watts for 10 minutes. The crosslinking process ensures uniform heating and prevents local overheating. Thus, the crosslinking reaction results in a homogeneously crosslinked product.

The following examples are provided to further illustrate the process of the present invention. These examples are illustrative only and are not intended to limit the scope of the invention in any way.

Examples 1 and 2 are comparative examples. Examples 3–5 were carried out according to the present invention.

EXAMPLES

Example 1

77.8 g of gelatin bloom number 140, 15.4 g fructose and 13.6 g glycerol were placed in a 500 ml double wall vessel. 100 ml of deionized water was added to the vessel and the mixture was brought into solution while stirring with a mincer disc at 1000 revolutions/minute (rpm) and approx. 65° C. This solution is called a matrix solution. Thereafter, a mixture of 39.4 g of crystalline vitamin A acetate, 2.8 million IU/g, and 10.2 g BHT (antioxidants) were emulsified in this matrix and stirred for 5 minutes. During the emulsification and stirring, the mincer disc was operated at 4800 rpm. After this emulsification, the internal phase of the emulsion had a average particle size of about 340 nm as measured by laser diffraction. The emulsion was diluted with 100 ml of deionized water and the temperature was maintained at 65° C.

Subsequently, 1300 g of corn starch (fluidized with silicic acid) were placed in a laboratory spray pan and cooled to at least 0° C. The emulsion was sprayed into the spray pan using a rotating spray nozzle. The thus-obtained particles coated with corn starch were sieved off (sieve fraction 0.16 to 0.63 mm) from the excess corn starch and dried at room temperature using a stream of air. 201 g of particles coated with corn starch were obtained which had outstanding flow properties, were completely dry and could be handled very well.

For heat treatment, 160 g of the above particles were placed in a 1000 ml glass beaker and put into an oil bed. During the heating at 135° C., the particles were stirred with a teflon stirrer (300 rpm). This heat treatment results in a cross-linking of the gelatin matrix (maillard reaction). The vitamin A content of the final product was 502,300 IU/g, the degree of cross-linking 91% and loss on drying was 2.8%. The cross-linking degree was determined by dispensing the product in water at 55° C. and a concentration of 4%. The thereby released vitamin A in % of the vitamin A content was determined as cross-linking degree.

Example 2

In an experiment analogous to Example 1, the fructose was replaced with xylose. The yield was 193 g, the vitamin A content was 577,050 IU/g, the cross-linking degree was 96% and loss on drying was 0.3%.

Example 3

Example 1 was repeated analogously, but with a addition of 4.0 g of a enzyme (Transglutaminase ACTIVA TI® from Ajinomoto, Japan) just before spraying the emulsion into the corn starch. After spraying the particles/emulsion mixture, the mixture was maintained at 35° C. for six hours. The enzymatically coated particles were sieved off from the excess corn starch and dried analogously to Example 1. The yield was 208 g with a vitamin A content of 475,500 IU/g, the degree of cross-linking was 57% and loss on drying was 5.7%.

Example 4

Two trials of Example 3 were mixed (total: 425 g). 160 g of this enzymatically crosslinked particles were heat treated similarly to Example 1. The vitamin A content of this product was 516,600 IU/g, the cross-linking degree was 93% and loss on drying was 0.3%.

Example 5

Instead of the heat treatment described in Example 1, 50 g particles with a vitamin A content of 800,000 IU/g were placed in a 250 round flask and heat treated for 10 minutes using a micro wave oven (LAVIS 1000 Multi Quant). During heat treatment at 1000 Watts the particles were stirred with a teflon stirrer. The vitamin A content after heat treatment was 727,800 IU/g, the degree of cross-linking was 85% and loss on drying was 1.1%.

All products described in Examples 3 through 5 had the same good industrially applicable properties as that of Examples 1 and 2.

The invention being thus described, it will be obvious that the same may be varied in many ways. Such variations are not to be regarded as a departure from the spirit and scope of the invention and all such modifications are intended to be included within the scope of the following claims.

What is claimed is:

1. A process for preparing beadlets containing fat soluble substances comprising:
   (a) forming an aqueous emulsion of a fat soluble substance, a gelatin, and a reducing agent;
   (b) converting the emulsion into a dry powder; and
   (c) crosslinking the gelatin matrix in the coated particles by exposing the coated particles to a radiation source.

2. A process according to claim 1 wherein the aqueous emulsion further comprises an antioxidant and/or a humectant.

3. A process according to claim 1 wherein the fat soluble substance is a fat soluble vitamin selected from the group consisting of vitamin A, D, E, K and derivatives thereof, a carotenoid, a polyunsaturated fatty acid, a flavoring agent and an aroma substance.

4. A process according to claim 3 wherein the fat soluble substance is vitamin A and its derivatives.

5. A process according to claim 4 wherein the fat soluble substance is vitamin A acetate or vitamin A palmitate.

6. A process according to claim 1 wherein the reducing agent is a reducing sugar or a reducing sugar derivative.

7. A process according to claim 6 wherein the reducing sugar is selected from the group consisting of glucose, fructose, galactose, mannose, talose, invert sugar, arabinose, ribose, xylose, lactose, maltose, and high fructose corn syrup.

8. A process according to claim 1 wherein the radiation source is microwaves.

9. A process according to claim 1 wherein the emulsion is converted into a dry powder by spray drying into a collecting powder.

10. A process according to claim 9 wherein the emulsion is converted into a dry powder by spray drying into a starchy powder.

11. A process according to claim 1 wherein the emulsion consists of:
    (a) about 1 wt % to about 80 wt % of a fat soluble substance;
    (b) about 5 wt % to about 70 wt % of gelatin;
    (c) about 2 wt % to about 20 wt % of a reducing agent;
    (d) optionally about 2 wt % to about 15 wt % of an antioxidant; and
    (e) optionally about 2 wt % to about 20 wt % of a humectant.

12. A process according to claim 11 wherein the emulsion consists of:
    (a) about 5 wt % to about 40 wt % of a fat soluble substance;
    (b) about 20 wt % to about 60 wt % of gelatin;
    (c) about 5 wt % to about 10 wt % of a reducing agent;
    (d) optionally about 5 wt % to about 10 wt % of an antioxidant; and
    (e) optionally about 5 wt % to about 10 wt % of a humectant.

13. A process for preparing beadlets containing fat soluble substances comprising:
    (a) forming an aqueous emulsion of a fat soluble substance, a gelatin, and a reducing agent;
    (b) converting the emulsion into a dry powder; and
    (c) crosslinking the gelatin matrix in the coated particles by incubating the coated particles in the presence of a crosslinking enzyme.

14. A process according to claim 10 wherein the enzyme is a transferase.

15. A process according to claim 14 wherein the transferase is a transglutaminase.

16. A process according to claim 15, wherein the transglutaminase is present in an amount from about 0.01 g/g to about 0.10 g/g gelatin.

17. A process according to claim 13 wherein the aqueous emulsion further comprises an antioxidant and/or humectant.

18. A process according to claim 13 wherein the fat soluble substance is a fat soluble vitamin selected from the group consisting of vitamin A, D, E, K and derivatives thereof, a carotenoid, a polyunsaturated fatty acid, a flavoring agent and an aroma substance.

19. A process according to claim 13 wherein the emulsion consists of:
    (a) about 1 wt % to about 80 wt % of a fat soluble substance;
    (b) about 5 wt % to about 70 wt % of gelatin;
    (c) about 2 wt % to about 20 wt % of a reducing agent;
    (d) optionally about 2 wt % to about 15 wt % of an antioxidant; and
    (e) optionally about 2 wt % to about 20 wt % of a humectant.

20. A process according to claim 19 wherein the emulsion consists of:
    (a) about 5 wt % to about 40 wt % of a fat soluble substance;
    (b) about 20 wt % to about 60 wt % of gelatin;
    (c) about 5 wt % to about 10 wt % of a reducing agent;
    (d) optionally about 5 wt % to about 10 wt % of an antioxidant; and
    (e) optionally about 5 wt % to about 10 wt % of a humectant.

* * * * *